(12) United States Patent
Hwang et al.

(10) Patent No.: US 8,859,272 B2
(45) Date of Patent: Oct. 14, 2014

(54) MICRO-DEVICE AND METHODS FOR DISRUPTING CELLS

(75) Inventors: Kyu-youn Hwang, Yongin-si (KR); Joon-ho Kim, Seongnam-si (KR); Sung-hong Kwon, Yongin-si (KR); Chin-sung Park, Yongin-si (KR); Hee-kyun Lim, Hwaseong-si (KR); Sun-ok Jung, Seongnam-si (KR); Won-jong Jung, Seongnam-si (KR)

(73) Assignee: Samsung Electronics, Ltd., Suwon-Si (KR)

( * ) Notice: Subject to any disclaimer, the term of this patent is extended or adjusted under 35 U.S.C. 154(b) by 68 days.

(21) Appl. No.: 13/275,871

(22) Filed: Oct. 18, 2011

(65) Prior Publication Data

US 2012/0107823 A1 May 3, 2012

(30) Foreign Application Priority Data

Oct. 29, 2010 (KR) ........................ 10-2010-0107014

(51) Int. Cl.
*C12M 1/33* (2006.01)
*C12Q 1/68* (2006.01)

(52) U.S. Cl.
CPC ...................................... *C12M 1/33* (2013.01)
USPC ........................................ 435/306.1; 435/6.1

(58) Field of Classification Search
None
See application file for complete search history.

(56) References Cited

U.S. PATENT DOCUMENTS

| | | | |
|---|---|---|---|
| 6,168,948 B1 * | 1/2001 | Anderson et al. | 435/287.2 |
| 6,440,725 B1 * | 8/2002 | Pourahmadi et al. | 435/288.5 |
| 2002/0019060 A1 * | 2/2002 | Petersen et al. | 436/514 |
| 2002/0148992 A1 * | 10/2002 | Hayenga et al. | 251/61.1 |
| 2003/0175947 A1 * | 9/2003 | Liu et al. | 435/288.5 |
| 2007/0224424 A1 * | 9/2007 | Tamori et al. | 428/403 |
| 2008/0014122 A1 | 1/2008 | Kim et al. | |
| 2008/0199930 A1 * | 8/2008 | Lee et al. | 435/173.1 |
| 2010/0167384 A1 | 7/2010 | Clemmens et al. | |

FOREIGN PATENT DOCUMENTS

| | | |
|---|---|---|
| CN | 101415813 A | 4/2009 |
| EP | 1 797 956 A1 | 6/2007 |
| WO | 03/015922 A1 | 2/2003 |
| WO | 03/015923 A1 | 2/2003 |
| WO | 2008/030631 A2 | 3/2008 |
| WO | 2008/104916 A2 | 9/2008 |
| WO | WO 2008104916 A2 * | 9/2008 |

OTHER PUBLICATIONS

Kim et al. (Microfluidic sample preparation: cell lysis and nucleic acid purification, Integr. Biol., 1, 574-586, published online Aug. 25, 2009).*
Taylor et al., Lysing Bacterial Spores by Sonication through a Flexible Interface in a Microfluidic System, Anal. Chem. 2001, 73, 492-496.*
Hwang et al., Miniaturized bead-beating device to automate full DNA sample preparation processes for Gram-positive bacteria, *Lab Chip*, 2011, 11: 3649-3655.
Kido et al., "A novel, compact disk-like centrifugal microfluidics system for cell lysis and sample homogenization," *Collides and Surface B: Biointerfaces*, 2007, 58: 44-51.
Kim et al, "Cell lysis in a microfluidic CD (compact disk)," *Lab Chip*, 2004, 4: 516-522.
Lin et al., "Cell lysis methods for high-throughput screening or miniaturized assays," *Biotechnology Journal*, 2009, 4: 210-215.
Weibel et al., "Microfabrication meets microbiology," *Nature Reviews: Microbiology*, 2007, 5: 209-218.
Chinese Office Action in Application No. 2011-10332898.9, issued Jun. 24, 2014.
Zhanglin et al., "Cell Lysis methods for high-throughput screening or miniaturized assays", *Biotechnology Journal*, vol. 4, No. 2, pp. 210-215 (2009).

* cited by examiner

*Primary Examiner* — Christopher M Babic
*Assistant Examiner* — Aaron Priest
(74) *Attorney, Agent, or Firm* — Leydig, Voit & Mayer, Ltd.

(57) ABSTRACT

A micro-device for disrupting cells includes a first chamber in which the cells are disrupted, a second chamber which is pressurized and depressurized, a flexible membrane which separates the first chamber and the second chamber and is vibrated by pressuring and depressurizing the second chamber, and a micro-unit confined in the first chamber, where the micro-unit disrupts the cells in the first chamber

17 Claims, 3 Drawing Sheets

MICRO-DEVICE AND METHODS FOR DISRUPTING CELLS

CROSS-REFERENCE TO RELATED APPLICATIONS

This application claims priority to Korean Patent Application No. 10-2010-0107014, filed on Oct. 29, 2010, and all the benefits accruing therefrom under 35 U.S.C. §119, the content of which in its entirety is herein incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 1,051 bytes ASCII (Text) file named "709313_SeqListing" created Dec. 27, 2011.

BACKGROUND

1. Field

The present disclosure relates to a device for disrupting cells, and more particularly, to a micro-device for disrupting cells and a method for disrupting cells using the micro-device.

2. Description of the Related Art

A nucleic acid-based micro total analysis system ("μTAS") is a promising platform for analyzing molecules. In such an analytic system, all analysis processes, e.g., a nucleic acid sample preparation process, an amplification process and a detection process, are integrated on a microchip and are automated. Real-time polymerase chain reaction ("PCR") process has been widely used since additional post-PCR analysis processes, e.g., electrophoresis and fluorescent imaging, may be omitted, thereby saving time and reducing complexity.

However, the sample preparation process for obtaining a nucleic acid suitable for PCR from a raw sample has not been effectively integrated into the entire analysis process on a microchip. Impurities in a sample may directly affect the specificity and sensitivity of PCR. Accordingly, elimination of impurities in a sample may substantially improve the amplification process.

Moreover, a target analyte in a sample is concentrated from an initial large volume to a small volume, and thus the initial sample having a volume of milliliters (ml) may be processed in the micro-device. Such a property improves PCR sensitivity, and is of great merit in using the micro-device beyond the capacities of laboratory equipment. Accordingly, inclusion of such functions in the device for nucleic acid preparation may substantially improve the application of the microfluidic analysis system.

The nucleic acid preparation process typically includes cell disruption for releasing nucleic acid from inside a cell to outside the cell. Cell disruption may include a process for disrupting cell membranes or cell walls. In particular, gram positive bacteria have a very thick peptidoglycan layer. Accordingly, it is more difficult to disrupt the cell membranes of gram positive bacteria than those of gram negative bacteria. *Staphylococcus aureus* ("*S. aureus*"), *Streptococcus pneumoniae*, and *Enterococcus* species, are examples of gram positive bacteria. An example of a *Staphylococcus aureus* species is methicillin-resistant *Staphylococcus aureus* ("MRSA") and *Enterococcus* species include Vancomycin-resistant *Enterococcus* ("VRE"). *Streptococcus pneumoniae* is a causative pathogen of, for example, pneumonia and sepsis.

SUMMARY

Provided is a micro-device for disrupting cells, which facilitates cell disruption.

Provided is a method for disrupting cells using the micro-device for disrupting cells.

Additional aspects will be set forth in part in the description which follows and, in part, will be apparent from the description, or may be learned by practice of the embodiments set forth herein.

According to an embodiment of the invention, a micro-device for disrupting cells includes a first chamber in which the cells are disrupted, a second chamber which is pressurized and depressurized, a flexible membrane which separates the first chamber and the second chamber and is vibrated by pressuring and depressurizing the second chamber, and a micro-unit confined in the first chamber, where the micro-unit disrupts the cells in the first chamber.

In an embodiment, the micro-unit may include a plurality of microbeads.

In an embodiment, the first chamber may include an inlet, through which the cells are introduced, and an outlet, through which contents of disrupted cells are released.

In an embodiment, the second chamber may include a plurality of sub-chambers.

In an embodiment, the plurality of microbeads may include at least one of a glass bead, a metallic bead and a metal oxide bead.

In an embodiment, the micro-unit may further include an organic layer disposed on a surface of the plurality of microbeads.

In an embodiment, the organic layer may include at least one of an antibody, an aptamer, a receptor, a ligand and organosilane.

In an embodiment, a diameter of each of the plurality of microbeads may be in a range of about 1 micrometer to about 500 micrometers.

In an embodiment, a density of the plurality of microbeads may be in a range of about 1 gram per cubic centimeter to about 20 grams per cubic centimeter.

In an embodiment, the metallic bead may include at least one of steel and stainless steel, and the metal oxide bead may include at least one of $ZrO_2$, $SiO_2$, $Al_2O_3$, $Fe_2O_3$ and $TiO_2$.

In an embodiment, a size of at least one of the inlet and the outlet may be less than a size of the micro-unit.

In an embodiment, a size of at least one of the inlet and the outlet may be greater than a size of the micro-unit, and the first chamber may further include at least one projection on an inner surface of the at least one of the inlet and the outlet, where the at least one projection makes an effective size of the at least one of the inlet and the outlet less than a size of the micro-unit.

In an embodiment, a thickness of the membrane may be in a range of about 1 micrometer to about 5 millimeters.

In an embodiment, the cells may include at least one of bacteria, virus and fungi.

According to another embodiment of the invention, a method of disrupting cells includes: introducing cells into a first chamber of a micro-device for disrupting cells, where the micro-device includes the first chamber, a second chamber which is pressurized and depressurized, a flexible membrane which separates the first chamber and the second chamber and is vibrated by pressurizing and depressurizing the second chamber, and a micro-unit for disrupting cells confined in the first chamber; disrupting the cells by vibrating the flexible membrane between the first chamber and the second chamber, after the introducing the cells; and releasing resultant disrupted cells from the first chamber of the micro-device.

In an embodiment, the introducing the cells may include passing a solution containing the cells through the first chamber.

In an embodiment, the method may further include providing a cell lysis solution to the first chamber.

In an embodiment, the disrupting of the cells may include vibrating the plurality of micro-units by vibrating the flexible membrane which separates the first chamber from the second chamber.

In an embodiment, the cell lysis solution may include at least one of NaOH, KOH, chaotrope, a surfactant, cell wall degrading enzyme and a biological buffer.

In an embodiment, the disrupting the cells may include periodically or non-periodically adjusting the pressure of the interior of the second chamber such that the flexible membrane is vibrated.

In an embodiment, the disrupting the cells may include vibrating the flexible membrane at a range of about 0.001 hertz to about 100 kilohertz.

In an embodiment, the method may further include disrupting the cells by vibrating the flexible membrane between the first chamber and the second chamber, after the introduction of the cells.

In an embodiment, the micro-unit may include a microbead.

According to another embodiment of the invention, a micro-device includes a membrane, a first chamber which is partly delimited by the membrane, a second in the first chamber, where the plurality of microparticles contacts the membrane, and a port in fluid communication with the second chamber, where the membrane is vibrated by pressurizing and depressurizing the second chamber.

In an embodiment, a density of the plurality of microparticles may be in a range of about 1 gram per cubic centimeter to about 20 grams per cubic centimeter.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
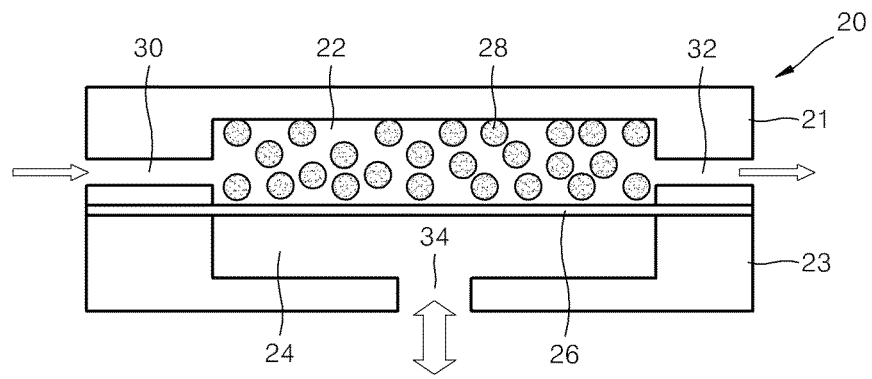
FIG. 1 is a cross sectional view of an embodiment of a micro-device for disrupting cells in a molecular diagnostic apparatus according to the invention.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, embodiments of the invention will be described in further detail with reference to the accompanying drawings.

Figure 2:
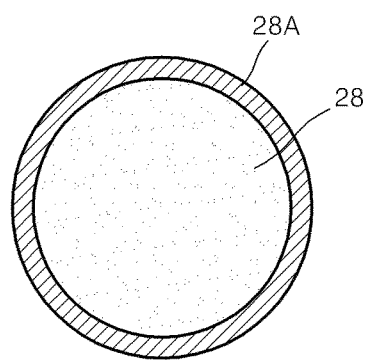
FIG. 2 is a cross section view of an embodiment of a bead including an organic layer thereon.

FIG. 1 is a cross sectional view of an embodiment of a micro-device for disrupting cells in a molecular diagnostic apparatus, and FIG. 2 is a cross section view of an embodiment of a bead including an organic layer thereon.

Referring to FIG. 1, the micro-device 20 includes an upper plate 21, a lower plate 23 and a membrane 26. The membrane 26 is disposed between the upper plate 21 and the lower plate 23. A space in a portion of the upper plate 21 defines a first chamber 22, and a space in a portion of the lower plate 23 defines a second chamber 24. The first chamber 22 and the second chamber 24 are separated by the membrane 26, disposed between the first chamber 22 and the second chamber 24. In such an embodiment, the first chamber 22 is delimited by the upper plate 21 and the membrane 26, and the second chamber 24 is delimited by the lower plate 23 and the membrane 26. In some embodiments, each of the first chamber and the second chamber may have a volume in a range from about 1 microliter (ul) to about 10,000 microliters (ul).

The membrane 26 may be flexible. In an embodiment, the membrane 26 may be a polymer membrane, such as polydimethylsiloxane ("PDMS") membrane, for example. The thickness of the membrane 26 may be, for example, in a range from about 1 micrometer (um) to about 5 millimeters (mm). The membrane 26 may be liquid and gas-permeable, but it may also be partly permeable.

The first chamber 22 may include a plurality of micro-units, e.g., a plurality of particles. The micro-units may be magnetic or non-magnetic micro-units. In an embodiment, the particles may be a plurality of beads 28, as shown in FIG. 1. Since the first chamber 22 is delimited by the membrane 26, the beads 28 may contact with the membrane 26. In an embodiment, the beads 28 may be microbeads. In the exemplary embodiment shown in FIG. 1, the micro-units include the plurality of beads 28, but the invention is not limited thereto. In an alternative embodiment, other units may be included in the first chamber 22 instead of the plurality of beads 28. In an embodiment, the diameter of each bead 28 may be, for example, in the range of about 1 um to about 500 um. The density of beads 28 in the first chamber 22 may be greater than about 1 gram per cubic centimeter (g/cm$^3$), for example, in the range of about 1 g/cm$^3$ to about 20 g/cm$^3$. In an embodiment, at least one bead may be included in the liquid medium, for example, there may be 10, 100, 1000, 10,000, 10$^5$, 10$^6$, 10$^7$, 10$^8$, or 10$^9$ or more beads per 1 microliter (ul) of the liquid medium. In some embodiments, 1 to 10$^8$ beads, for example, 100 to 10$^6$ beads, may be included per 1 ul of the liquid medium in the first chamber 22. The micro-units may have a sphere shape, a plate shape, or may have a shape including a plurality of sides. The micro-units may be magnetic or non-magnetic beads. In an embodiment, the beads 28 may be glass beads. In an alternative embodiment, the beads 28 may be metal oxide beads or metallic beads.

The metal oxide may be one of $ZrO_2$, $SiO_2$, $Al_2O_3$, $Fe_2O_3$, $TiO_2$ and a mixture thereof. In one embodiment, the mixture may be, for example, a mixture including $ZrO_2$ and $SiO_2$. The metal beads may be, for example, formed of steel or stainless steel. In an embodiment, the beads 28 have a composition of glass or metal oxide, and surface modifications for cell capture or absorption are thereby effectively implemented.

In an embodiment, surfaces of the beads 28 may be capable of binding to a cell or may be modified to be suitable for cell capture by binding to a cell. The surfaces of the beads 28 may be hydrophobic, for example, have a water contact angle in a range of 70° to 95°. The hydrophobicity may be rendered, for example, by coating the surfaces of the beads 28 with compounds such as octadecyldimethyl(3-trimethoxysilylpropyl) ammonium ("OTC") or tridecafluoro tetrahydrooctyltrimethoxysilane ("DFS"). The surfaces of the beads 28 may also be coated with polyethyleneimine trimethoxy silane ("PEIM"). The surfaces of the beads 28 may have cell-binding substances immobilized thereon, such as an antibody which binds to an antigen on a cell surface, a receptor which binds to a ligand on a cell surface, or a ligand which binds to a receptor on a cell surface, for example. In an embodiment, the surfaces of the beads 28 include substances capable of specifically binding to specific cells such that the beads 28 specifically separate specific cells. In an alternative embodiment, the surfaces of the beads 28 include substances capable of non-specifically binding to cells such that the beads 28 non-specifically separate all kinds of cells.

The cells may include bacteria, a virus or fungi. The cells may be contained in an appropriate liquid medium. The liquid medium may be, for example, a medium for cell culture, a buffer, for example, phosphate buffered saline ("PBS"), physiological saline, body fluids or water. The liquid medium may also include a cell lysis solution. The cell lysis solution may be additionally and separately supplied to the chamber after the liquid medium containing the cells is supplied, or may be pre-mixed and then supplied to the chamber. The cell lysis solution may include a non-specific cell lysis agent and/or a specific cell lysis agent. The non-specific cell lysis agent may include at least one of a surfactant, NaOH and a chaotropic salt. The specific cell lysis agent may include, cell wall degrading enzyme for example, lysozyme, lysostaphin or penicillin and beta-lactam antibiotics.

The cells bound to the micro-units may be washed, after the cells are introduced into the first chamber 22. The washing may be carried out by passing a wash solution through the first chamber 22 with or without the liquid medium. The wash solution may wash off unbound substances, leaving the cells bound to the micro-units. The wash solutions may be, for example, water, a buffer (such as a PBS buffer) or physiological saline.

In one embodiment, the cells may be disrupted while the cells are introduced into the first chamber 22. In an alternative embodiment, the cells may be disrupted after the cells are introduced into the first chamber 22.

The micro-device 20 includes an inlet 30 and an outlet 32. The sizes of the inlet 30 and outlet 32 may be smaller than a size of the micro-units, e.g., a diameter of each bead 28. In one exemplary embodiment, the inlet 30 and the outlet 32 may have a circular cross-sectional shape, and the diameters of the inlet 30 and the outlet 32 may be less than the diameter of the bead 28. A solution containing cells to be disrupted is introduced into the first chamber 22 through the inlet 30. Resultant disrupted cells, including a nucleic acid, for example, obtained by the disruption of cell membrane and/or walls are released through the outlet 32. The inlet 30 may be formed through one wall of the upper plate 21 to connect to one side of the first chamber 22. The outlet 32 may be formed through another wall of the upper plate 21 to connect to the other side of the first chamber 22.

In an embodiment, at least one of the inlet 30 and outlet 32 may be operatively connected to a unit for providing power (not shown). The unit for providing power can provide a power to move a fluid through at least one of the inlet 30 and outlet 32. The unit for providing power may include a unit causing the motion of fluid, for example, a unit that provides a positive pressure or a negative pressure to the first chamber 22, including a pump. The pump may be a micropump, which may be applied to a microfluidic device. The micropump may be a mechanical or a non-mechanical device. The mechanical micropump may include an actuator and moving parts which are membranes or flaps. The motion of fluid may be generated using a piezoelectric, electrostatic, thermo-pneumatic, pneumatic or magnetic effect. A non-mechanical device may function as the unit for providing the power by generating an electro-hydrodynamic force, or an electro-osmotic or ultrasonic flow.

The inlet 30 and the outlet 32 may be in fluid-communication with the first chamber 22, for example, through a microchannel (not shown). The microchannel may have a width in a range of about 1 um to about 10,000 um, for example about 1 um to about 5,000 um.

The first chamber 22 including the micro-units may be in fluid-communication with at least one of a storage unit (not shown) that stores a cell lysis solution and a storage unit (not shown) that stores cell wash solution. The storage units may be connected to the chamber through the inlet 30. The cells may be introduced by applying a positive pressure to an inlet 30 of the first chamber 22 or applying a negative pressure to the outlet 32 of the first chamber 22. In an embodiment, the negative pressure or positive pressure may be applied by a pump (not shown). The pump may be at least one of a peristaltic pump and a pneumatic pump. In an alternative embodiment, the cells may be introduced through direct infusion by a user. In one embodiment, for example, the cells may be infused by the user performing pipetting. The amount and rate of introduction may depend on the cells to be disrupted, the purpose of cell disruption, and the post-cell disruption process, for example, and one of ordinary skill in the art may appropriately adjust them. The application of the pressure may be carried out in a state in which both the inlet 30 and the outlet 32 are closed. That is, the cells may be disrupted in a closed chamber containing the cells. The application of the pressure may be also carried out in a state in which at least one of the inlet 30 and the outlet 32 is open. That is, the cells may be disrupted under conditions that at least a portion of the liquid medium containing the cells in the chamber is flowing.

The second chamber 24 may operate as a pneumatic chamber including a space into which a fluid, such as air, for pressing periodically or non-periodically on the membrane 26 is introduced. High-pressurized fluid is introduced into the second chamber 24, and thus the membrane 26 is pressed. When the membrane 26 is pressed, the membrane 26 protrudes toward the first chamber 22, and the spatial volume of the first chamber 22 is thereby reduced. When the membrane 26 is depressed, the membrane 26 shrinks down toward the second chamber 24. The second chamber 24 has a port 34 which is an inflow passage of the fluid that pressurizes the interior of the second chamber 24 and simultaneously is an outflow passage of the fluid. In an embodiment, the fluid may be periodically or non-periodically introduced into/the second chamber 24 through the port 34 or released from the second chamber 24 through the port 34, and thus the membrane 26 may be periodically or non-periodically vibrated. The vibration of the membrane 26 leads to a periodic or non-periodic pressure to the beads 28 in the first chamber 22 through direct contact with the beads 28 or through the solution contained in the first chamber 22. In such an embodiment, motion of the beads 28 is induced, and the beads 28 collide with each other or collide with an inner wall of the first chamber 22. Due to the motion of the beads 28, the cells introduced into the interior of the first chamber 22 are disrupted by being sheared or grinded, that is the cells may be disrupted by a shearing force or an impact force applied to the cell or by heat, which are induced by the motion of the micro-units. The pressurizing or depressurizing of the interior of the second chamber 24 through the introduction of the fluid into the second chamber 24 (applying a positive pressure) or release of the fluid from the second chamber 24 (applying a negative pressure) is effectively controlled with a vibration frequency in a range of from about 0.001 hertz (Hz) to about 100 kilohertz (kHz).

Referring to FIG. 2, surfaces of the beads 28 may have an organic layer 28A which allows for specific or non specific cell capture. In one embodiment, for example, an antibody or an aptamer, may be coated on the surfaces of the beads 28 to selectively capture a specific cell. In an embodiment, a non-specific cell may be captured by a hydrophobic or electrostatic force.

The organic layer 28A may be formed by modifying the surfaces of beads 28 in various ways using organosilane.

In one embodiment, a portion having an affinity with a specific or nonspecific cell is on a surface of the beads 28, and the cells introduced into the first chamber 22 are captured by the portion on the surface of the beads 28. In such an embodiment, the vibration of the membrane 26 causes the motion of the beads 28, which makes beads collide with each other or with the inner surface of the wall of the first chamber 22, and the cells on the surface of the beads 28 may be disrupted by the collisions.

In an alternative embodiment, after supplying a solution containing the cells to be disrupted, a substance for increasing the cell disruption effect may be supplied in the first chamber 22, and then the cell disruption may be carried out. In an embodiment, the cell lysis solution may include the substance for increasing the cell disruption effect. The cell lysis solution may include, for example, NaOH, KOH, a chaotropic solution or a surfactant. In an embedment, the cell lysis solution may include a biological buffer such as Tris, phosphate, citrate, acetate and carbonate, for example, which does not increase the cell disruption effect. The cell lysis solution may be used in a concentration not affecting the post-cell disruption processes such as polymerase chain reaction ("PCR"), and thus PCR may be conducted after cell disruption without a further purification process. In such an embodiment, the substance is used in a concentration affecting PCR, and then a purification process is carried out. The cell lysis solution may be supplied after the cell disruption process, thereby facilitating the release of a nucleic acid.

In an alternative embodiment, a solution containing the cells may be supplied to the first chamber 22 and then the cell disruption may be carried out without additional supply of the cell lysis solution into the chamber 22.

FIGS. 3 to 6 are cross sectional views of alternative embodiments of the micro-device for disrupting cells in a molecular diagnostic apparatus according to the invention.

Figure 3:
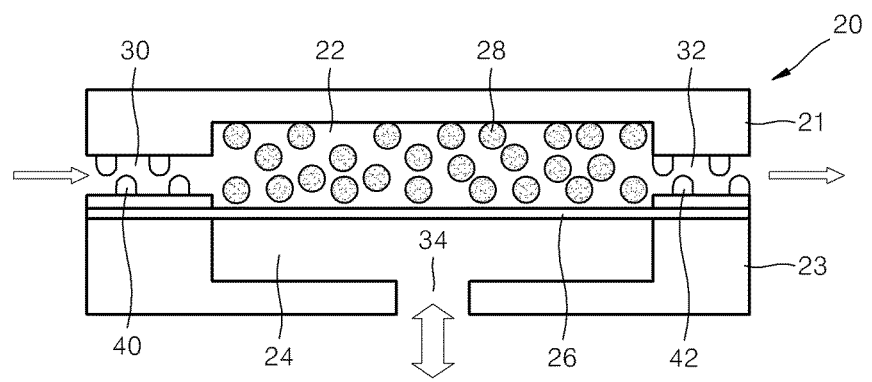
FIGS. 3 to 6 are cross sectional views of alternative embodiments of the micro-device for disrupting cells in a molecular diagnostic apparatus according to the invention.

FIG. 3 shows an alternative embodiment of the micro-device 20 of FIG. 1. The micro-device in FIG. 3 is substantially the same as the micro-device shown in FIG. 1 except for the inlet 30 and the outlet 32. The same or like elements shown in FIG. 3 have been labeled with the same reference characters as used above to describe the embodiment of the micro-device shown in FIG. 1, and any repetitive detailed description thereof will hereinafter be omitted or simplified.

Referring to FIG. 3, the sizes of the inlet 30 and the outlet 32 may be larger than a size of the bead 28. In one exemplary embodiment, the inlet 30 and the outlet 32 may have a circular cross-sectional shape, and the diameters of the inlet 30 and the outlet 32 may be greater than the diameter of the bead 28. A plurality of first projections 40 is disposed on an inner side of the inlet 30. The first projections 40 may be evenly distributed throughout the inner side of the inlet 30. The first projections 40 may be disposed in opposite direction with each other. Due to the first projections 40, the substantial size or effective size of the inlet 30, e.g., a size of a cross-sectional shape of the inlet 30 becomes smaller than the size of the beads 28. Similarly, a plurality of second projections 42 is disposed the inner side of the outlet 32. The distribution of the second projections 42 may be substantially the same as the distribution of the first projections 40. Due to the second projections 42, the substantial size or effective size of the outlet 32, e.g., a size of a cross-sectional shape of the outlet 32, may be smaller than the size of each bead 28. In an embodiment, the shapes of the first and second projections 40 and 42 may be substantially identical to each other. In an alternative embodiment, the shapes of the first and second projections 40 and 42 may be substantially different from each other. In an embodiment, the first and second projections 40 and 42 may be formed by embossing the inner sides of the inlet 30 and the outlet 32.

Figure 4:
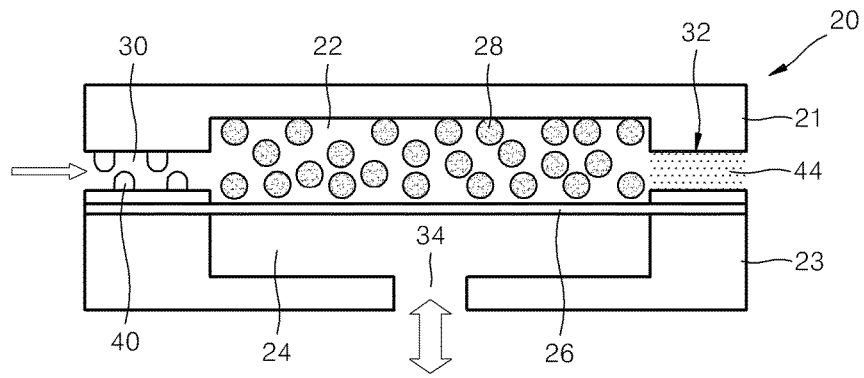

FIG. 4 shows another alternative embodiment of the micro-device 20 of FIG. 1. The micro-device in FIG. 4 is substantially the same as the micro-device shown in FIG. 1 except for the inlet 30 and the outlet 32. The same or like elements shown in FIG. 4 have been labeled with the same reference characters as used above to describe the embodiment of the micro-device shown in FIG. 1, and any repetitive detailed description thereof will hereinafter be omitted or simplified.

Referring to FIG. 4, the inlet 30 may be substantially the same as the inlet 30 of the embodiment shown in FIG. 3. In an embodiment, a filter 44 may be disposed in the outlet 32. The filter 44 may be a porous material which allows contents of the disrupted cells to pass. The size of the inlet 30 may be smaller than the size of the micro-unit, e.g., the size of each bead 28, as in FIG. 1.

Figure 5:
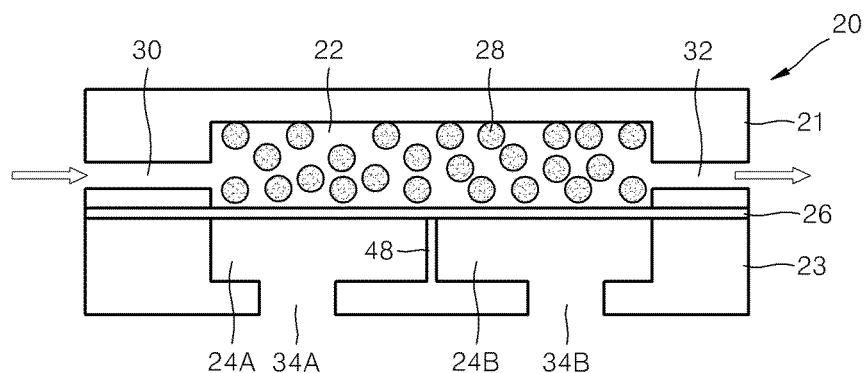

FIG. 5 shows another alternative embodiment of the micro-device 20 of FIG. 1. The micro-device in FIG. 5 is substantially the same as the micro-device shown in FIG. 1 except for the second chamber 24. The same or like elements shown in FIG. 5 have been labeled with the same reference characters as used above to describe the embodiment of the micro-device shown in FIG. 1, and any repetitive detailed description thereof will hereinafter be omitted or simplified Referring to FIG. 5, the second chamber 24 includes two chambers, e.g., a first sub-chamber 24A and a second sub-chamber 24B. The first sub-chamber 24A and the second sub-chamber 24B are separated by a partition wall 48. The role of the third and second sub-chambers 24A and 24B may be the same as that of the second chamber 24. The first sub-chamber 24A includes a first port 34A, and the second sub-chamber 24B includes a second port 34B. The structure of the first port and second port 34A, 34B may be substantially the same as the structure of the port 34 in the second chamber 24 of the embodiment shown in FIG. 1. The structural of the inlet 30 and the outlet 32 may be substantially the same as to the inlet and the outlet 32 of the embodiments shown in FIG. 3 or FIG. 4. The pressure may be applied to the first and second ports 34A and 34B, simultaneously or sequentially such that the membrane 26 of each sub-chamber vibrates simultaneously or sequentially. In an embodiment, the pressure may be applied with a same phase of pressure or different phases of pressure to the first and second ports 34A and 34B such that the first and second sub-chambers 24A and 24B vibrate in the same phase or different phases. In one embodiment, for example, the positive pressure is applied to the first port 34A and the negative pressure is applied to the second port 34B, and the membrane 26 of the first sub-chamber 24A and the membrane 26 of the second sub-chamber 24B thereby vibrate in opposite phases.

Figure 6:
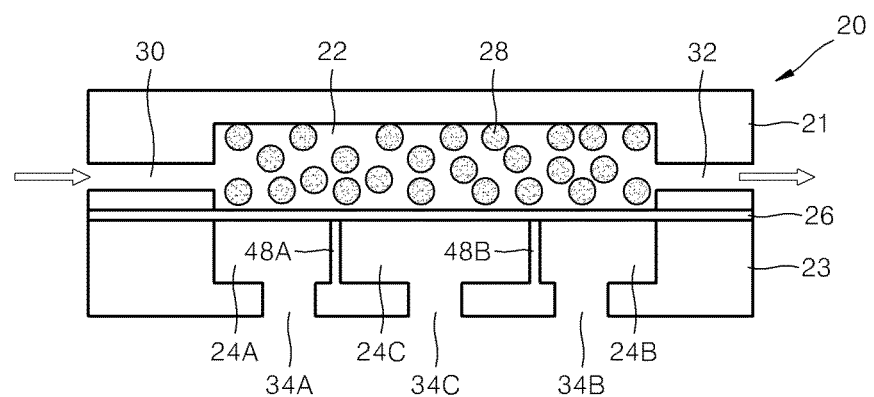

FIG. 6 shows another alternative embodiment of the micro-device 20. The micro-device in FIG. 6 is substantially the same as the micro-device shown in FIG. 1 except for the second chamber 24. The same or like elements shown in FIG. 6 have been labeled with the same reference characters as used above to describe the embodiment of the micro-device shown in FIG. 1, and any repetitive detailed description thereof will hereinafter be omitted or simplified Referring to FIG. 6, the second chamber 24 includes three sub-chambers, i.e., first to third sub-chambers 24A, 24B and 24C. The first to third sub-chambers 24A, 24B and 24C may perform a function substantially the same as the function that the second chamber 24 in FIG. 1 performs. The first sub-chamber and the third sub-chamber 24A and 24C are separated by a first partition wall 48A. The second sub-chamber and the third sub-chamber 24B and 24C are separated by a second partition wall 48B. The first to third sub-chambers 24A, 24B and 24C include first to third ports 34A, 34B and 34C, respectively. The structure and function of the first to third ports 34A 34B, and 34C may be substantially the same as the structure and function of the port 34 in FIG. 1. The second chamber 24 of the embodiment in FIG. 6 includes three sub-chambers, but the invention is not limited thereto. In an alternative embodiment, the second chamber 24 may include more than three sub-chambers. The pressure may be applied to the first to third ports 34A, 34B and 34C simultaneously or sequentially, allowing the membrane 26 in each chamber to vibrate simultaneously or sequentially. Also, the pressure may be applied at a same or different phase of pressure to the first to third ports 34A, 34B and 34C, enabling the membrane 26 of each chamber to vibrate in the same or different phase. In one embodiment, for example, the positive pressure may be applied to the first port 34A and the third port 34C, and the negative pressure may be applied to the second port 34B, such that the membrane 26 in the first sub-chamber and the third sub-chamber 24A and 24C and the membrane 26 in the second sub-chamber 24B vibrate in opposite phases to one another.

In the embodiments shown in FIGS. 1 and 3 to 6, the first chamber 22 is disposed above the second chamber 24, e.g., the first chamber 22 is an upper chamber and the second chamber 24 is a lower chamber, the invention is not limited thereto. In an alternative embodiment, the second chamber 24 may be disposed above the first chamber 22, e.g., the second chamber 24 may be the upper chamber and the first chamber 22 may be the lower chamber. The operations of the micro-device where the second chamber 24 is disposed above the first chamber 22 is substantially the same as the embodiments shown in FIGS. 1 and 3 to 6 where the first chamber 22 is disposed above the second chamber 24.

Hereinafter, the invention will be described with reference to the following examples. It should be understood that the exemplary embodiments described herein should be considered in a descriptive sense only and not for purposes of limitation.

EXAMPLE

1. Manufacture of a Micro-Device

A micro-device having three layers (e.g., glass layer-PDMS layer-glass layer) was manufactured. A channel and a chamber were formed on the glass wafer through conventional photographic and etching processes and a wet etching process.

After cleaning a 6 inch glass wafer (borosilicate glass, 700 um thickness) in a Piranha solution, e.g., a mixture of sulfuric acid ($H_2SO_4$) and hydrogen peroxide ($H_2O_2$), an amorphous polysilicon layer was vapor-deposited on the cleaned glass wafer to a thickness of 2000 um. Then, a patterning process was implemented, in which a part of the vapor-deposited polysilicon layer is exposed using a photoresist film. Then, the exposed part of the polysilicon layer was removed by dry etching. Thereafter, the photoresist film was stripped, and the exposed glass wafer was wet etched with a hydrofluoric acid solution (HF, 49%) to form a channel having a depth of 100 um and a width of 100 um. In the etching process to form the channel, a weir (projection) in a length of about 20 um was formed for isolating a bead. Next, the polysilicon layer was removed, and a dry film resist was coated and patterned. Then, a chamber (ca. 15.5 uL) for enclosing beads and holes were formed using a sand-blasting method. Thereafter, the glass wafer was diced into chip-shaped pieces, and cleaned with plasma. Then, a fluidic chip including the above-manufactured chamber in which beads are to be enclosed and a pneumatic chip including a chamber not enclosing the beads but functioning as a pneumatic pump were coupled to each other by way of a PDMS membrane (250 um thick) as an intermediate layer.

About 15 mg to about 16 mg (about $2 \times 10^5$ in number) surface-modified glass beads were put into the produced bead chamber, the chamber was sealed using a tape, and the tape was covered with a plastic substrate to prevent the bending thereof upon operation. The surface-modified glass beads may be directly put into the bead chamber.

Pressurizing and depressurizing the pneumatic chamber for vibrating the PDMS membrane and the motion of solution were controlled by a solenoid valve, an electro-regulator and LabVIEW software.

2. Modification of a Glass Bead

After cleaning a glass bead (diameter: about 30 um to about 50 um, Polysciences, Inc.) in a Piranha solution, e.g., a mixture of sulfuric acid ($H_2SO_4$) and hydrogen peroxide ($H_2O_2$), the glass bead was sufficiently washed with distilled water and filtered under vacuum until dry. The glass bead may be spherical.

Next, the bead was put into ethanol having 5 volume percent (% v/v) trimethoxysilylpropyl-modified (polyethyleneimine) (Gelest, Inc.) and a reaction was allowed to take place while mixing.

After about 2 hours, the glass bead was sufficiently washed with an ethanol solution and filtered under vacuum until dry. Then it was sintered in an oven at 110° C. for 40 minutes. As a result, a glass bead having a surface coated with polyethyleneimine ("PEIM") was obtained. Since the PEIM is capable of non-specifically binding to a cell, the glass bead may be employed for non-specifically separating a cell.

3. Experiments for Extracting a Nucleic Acid

Gram-positive bacteria of *S. aureus* ("SA") were diluted in a sodium acetate buffer (50 mM, pH 4) to a concentration of $10^6$ colony-forming units per milliliter (CFU/ml).

Then, 1 mL of the SA solution was introduced into a bead chamber by flowing through a channel, which is an inlet, to the chamber, at a flow rate of 200 ul/min for 5 minutes. The process was conducted with both the inlet and outlet of the chamber open.

Then, a Tris buffer (Tris, pH 8, 10 mM) for washing the bead chamber was flowed through the channel and the chamber, at a flow rate of 200 microliters per minute (ul/min), and subsequently air was injected for drying the beads.

Lastly, after injecting 0.02 N NaOH solution (6 uL) into the bead chamber at a very low rate, e.g., 30 kilopascal (kPa), the inlet and outlet were closed, and cells were disrupted by vibrating the PDMS membrane at a frequency of 10 Hz with +80 kPa and −80 kPa, by adjusting the Solenoid valve by means of the LabVIEW program. After the cell disruption process, the inlet and outlet were opened, 100 kPa of pressure was applied, 14 ul of NaOH solution was additionally injected, and then the cell disruption product was recovered through the outlet. Thus, a cell disruption product containing nucleic acid in a total of 20 ul of NaOH solution was obtained. For a positive control sample, a benchtop bead beating process was conducted.

As the positive control experiment, 1 ml of SA dilute solution, which was prepared for the subject experiment, was centrifuged at 13200 revolutions per minute (rpm) for 20 minutes to precipitate SA bacteria, and then the supernatant was removed. A volume of 20 μL of 0.02N NaOH, the same cell lysis solution used in the device, and glass beads were put into a container including the precipitated bacteria and mixing was carried out with a vortexer (GENIE 2, Fisher) at maximum speed (Max. 3200 rpm) for 5 minutes, to obtain a cell disruption product.

For a negative control, the supernatant was removed after centrifugation, deionized ("DI") water alone was put into the container including the precipitated bacteria, and mixing was carried out with the above vortexer at the maximum speed for 5 minutes.

4. Real-Time Polymerase Chain Reaction ("PCR")

The amount of DNA extracted from the cell disruption achieved using the embodiment of the device disclosed herein for actuation times up to 20 min was compared with the amount of DNA extracted from the positive control sample by means of PCR (TMC PCR machine, Samsung). An SA 442 region present in *S. aureus* was tested using the following primers (Applied Biosystems, US), probes and composition of the PCR.

TABLE 1

|  | Sequence |
|---|---|
| Sa442 forward primer | 5'-GTT GCA TCG GAA ACA TTG TGT T-3' (SEQ.ID.No. 1) |
| Sa442 reverse primer | 5'-ATG ACC AGC TTC GGT ACT ACT AAA GAT-3' (SEQ.ID.No. 2) |
| Sa442 Taqman probe | 5'-TGT ATG TAA AAG CCG TCT TG-3' (SEQ.ID.No. 3) |

TABLE 1-continued

| Component | volume (μl) | Final concentration |
|---|---|---|
| 10x Z-Taq buffer | 0.2 | 1x |
| 25 mM dNTP | 0.16 | 2 mM |
| Z-Taq polymerase | 0.02 | 0.5 U |
| 50 mM forward primer | 0.03 | 1 μM |
| 50 mM reverse primer | 0.03 | 1 μM |
| 20 mM probe | 0.03 | 0.4 μM |
| Water | 0.5 | — |
| Disrupted cell solution | 1 | — |

5. Experimental Results

Figure 7:
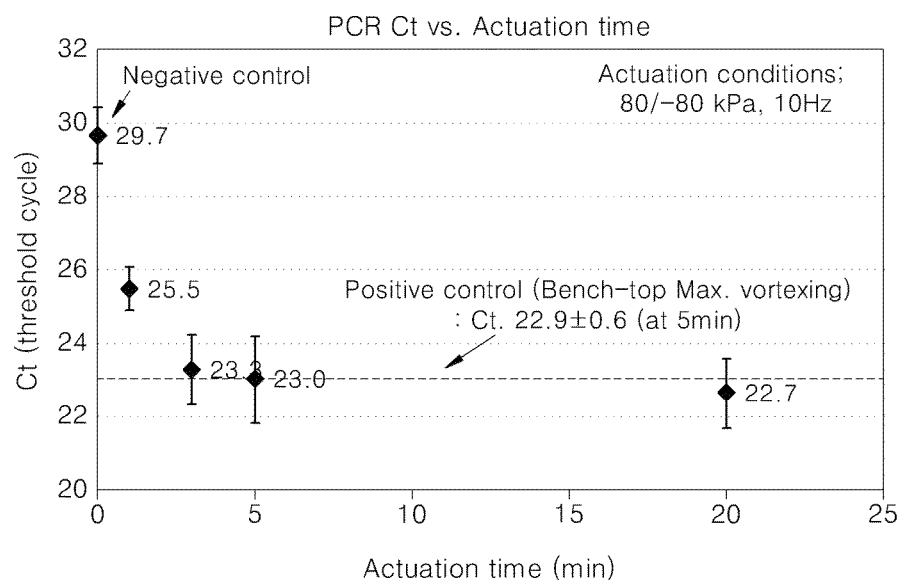
FIG. 7 is a graph showing threshold cycle (number) versus actuation time (minute) representing results of a cell disruption test conducted according to a method of disrupting cells.

The implementation of the cell disruption device and method for five minutes resulted in a similar threshold cycle (Ct) to that obtained in the positive control experiment, as shown in FIG. 7. Based on the experimental results shown in FIG. 7, it may be concluded that an embodiment of the method of disrupting cells according to the invention has similar performance to the performance of the bench top bead beating method, which is well known in the art.

In FIG. 7, the horizontal axis represents the actuation time, i.e., the time taken to disrupt cells in the device, and the longitudinal axis represents Ct.

An embodiment of the micro-device for disrupting cells according to the invention facilitates the disruption of cell membranes or cell walls by beating with microbeads. Therefore, the efficiency of elution of a particular substance in a cell, such as a nucleic acid, substantially increases, while the time for preparation of a sample, such as a nucleic acid preparation for a diagnostic assay, and the cost of the diagnostic assay are substantially reduced. In such an embodiment, the micro-device may be used in various diagnostic tools, such as a PCR apparatus, a microarray apparatus and a sequencing apparatus, for example, thereby increasing the accuracy of the diagnosis performed by the various diagnostic tools.

It should be understood that the embodiments described herein should be considered in a descriptive sense only and not for purposes of limitation. Descriptions of features or aspects within each embodiment should typically be considered as available for other similar features or aspects in other embodiments.

What is claimed is:

1. A method of disrupting cells, the method comprising:
introducing the cells into a first chamber of a micro-device for disrupting cells, wherein the micro-device comprises:
the first chamber;
a second chamber, which is pressurized and depressurized by flowing a fluid into and out of the second chamber through a port;
a flexible membrane which-separates the first chamber and the second chamber and is vibrated by pressurizing and depressurizing the second chamber; and
a micro-unit for disrupting cells confined in the first chamber;
disrupting the cells by vibrating the flexible membrane between the first chamber and the second chamber, after the introducing the cells; and
releasing resultant disrupted cells from the first chamber of the micro-device;
wherein the flexible membrane is vibrated by periodically or non-periodically adjusting the pressure of the interior of the second chamber such that the flexible membrane is vibrated, wherein the micro-device comprises:
an upper plate with a space defining the first chamber; and
a lower plate with a space defining the second chamber;
wherein the flexible membrane is disposed between the upper plate and the lower plate, the first chamber is delimited by the upper plate and the flexible membrane, and the second chamber is delimited by the lower plate and the flexible membrane.

2. The method of claim 1, wherein the introducing the cells comprises passing a solution containing the cells through the first chamber.

3. The method of claim 1, further comprising providing a cell lysis solution to the first chamber.

4. The method of claim 1, wherein the disrupting the cells comprises vibrating the micro-units by vibrating the flexible membrane.

5. The method of claim 3, wherein the cell lysis solution comprises at least one of NaOH, KOH, chaotrope, a surfactant, cell wall degrading enzyme and a biological buffer.

6. The method of claim 4, wherein the disrupting the cells comprises vibrating the flexible membrane at a range of about 0.001 hertz to about 100 kilohertz.

7. The method of claim 1, wherein the micro-unit comprises a microbead.

8. The method of claim 2, wherein the introducing the cells further comprises providing a cell lysis solution to the first chamber after the passing the solution containing the cells through the first chamber.

9. The method of claim 1, wherein the micro-unit comprises a plurality of microbeads.

10. The method of claim 1, wherein the first chamber comprises:
an inlet, through which the cells are introduced; and
an outlet, through which contents of disrupted cells are released.

11. The method of claim 9, wherein the plurality of microbeads comprises at least one of a glass bead, a metallic bead, and a metal oxide bead.

12. The method of claim 9, wherein the plurality of microbeads each further comprises an organic layer disposed on a surface thereof.

13. The method of claim 12, wherein the organic layer comprises at least one of an antibody, an aptamer, a receptor, a ligand, and organosilane.

14. The method of claim 11, wherein the metallic bead comprises at least one of steel and stainless steel, and the metal oxide bead comprises at least one of $ZrO_2$, $SiO_2$, $Al_2O_3$, $Fe_2O_3$, and $TiO_2$.

15. The method of claim 10, wherein a size of at least one of the inlet and the outlet is less than a size of the micro-unit.

16. The method of claim 1, wherein the cells include at least one of bacteria, virus and fungi.

17. The method of claim 1, wherein increasing pressure within the second chamber reduces the volume of the first chamber.

* * * * *

SEQUENCE LISTING

```
<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: Sa442 forward primer

<400> SEQUENCE: 1
gttgcatcgg aaacattgtg tt                                            22

<210> SEQ ID NO 2
<211> LENGTH: 27
<212> TYPE: DNA
<213> ORGANISM: Artificial Sequence
<220> FEATURE:
<223> OTHER INFORMATION: Sa442 reverse primer

<400> SEQUENCE: 2
atgaccagct tcggtactac taaagat                                       27

<210> SEQ ID NO 3
<211> LENGTH: 20
<212> TYPE: DNA
```

```
<213> ORGANISM: Artificial Sequence
<220> FEATURE:
<223> OTHER INFORMATION: Sa442 Taqman probe

<400> SEQUENCE: 3
tgtatgtaaa agccgtcttg                                              20
```